United States Patent
Sabata et al.

(10) Patent No.: US 7,526,944 B2
(45) Date of Patent: May 5, 2009

(54) REMOTE MONITORING OF PIPELINES USING WIRELESS SENSOR NETWORK

(76) Inventors: Ashok Sabata, 1184 Ocean Ave., D-4, Sea Bright, NJ (US) 07760; Sean Brossia, 21527 Rio Colorado, San Antonio, TX (US) 78259

( * ) Notice: Subject to any disclaimer, the term of this patent is extended or adjusted under 35 U.S.C. 154(b) by 0 days.

(21) Appl. No.: 10/905,488

(22) Filed: Jan. 6, 2005

(65) Prior Publication Data
US 2005/0145018 A1    Jul. 7, 2005

Related U.S. Application Data

(60) Provisional application No. 60/481,868, filed on Jan. 7, 2004.

(51) Int. Cl.
*G01M 3/28* (2006.01)
*G01N 17/00* (2006.01)

(52) U.S. Cl. .................. 73/49.1; 73/40.5 R; 73/86; 73/865.9; 702/113

(58) Field of Classification Search .............. 73/49.1, 73/40.5 R, 40.5 A, 865.9, 86; 702/113
See application file for complete search history.

(56) References Cited

U.S. PATENT DOCUMENTS

| | | | | |
|---|---|---|---|---|
| 4,066,095 A | * | 1/1978 | Massa | 137/486 |
| 6,957,157 B2 | * | 10/2005 | Lander | 705/56 |
| 2003/0204371 A1 | * | 10/2003 | Sciamanna | 702/183 |
| 2004/0233043 A1 | * | 11/2004 | Yazawa et al. | 340/10.3 |

OTHER PUBLICATIONS

Definition: Mesh Network; searchnetworking.techtarget.com, Sep. 19, 2003.*

* cited by examiner

*Primary Examiner*—Daniel S Larkin

(57) ABSTRACT

A wireless sensor network is installed inside pipelines using sensors and wireless transceivers that are small, low-cost, and rugged. The objective is monitoring the pipeline and recommending maintenance and repair at specific locations in the pipeline. Maintenance includes detection of internal corrosion using sensors that can result in leaks. Furthermore detection of leaks for prevention of catastrophic failures as a result of damage, such as third party mechanical damage. After establishing the wireless sensor network, the network is activated so the sensors can make measurements periodically or continuously using instructions transmitted via a base station. The sensor data from the various sensors are transmitted inside the pipe and extracted to access points in the pipeline to a remote computer that stores the data within the computer. The sensed information can be used for monitoring as well as analysis using a recommendation engine to provide maintenance and repair alerts.

12 Claims, 2 Drawing Sheets

Motes being deployed by a rolling the spherical sensor package inside the pipeline Motes being deployed by a rolling the spherical sensor package inside the pipeline Motes being deployed by a robot moving inside the pipeline Motes being deployed by a rolling the spherical sensor package inside the pipeline

REMOTE MONITORING OF PIPELINES USING WIRELESS SENSOR NETWORK

BACKGROUND OF THE INVENTION

Considerable expense and effort is currently employed in the energy and chemical processing sectors to conduct necessary inspections of pipelines and other piping systems (e.g., cooling water and process stream piping). Often, these inspections require system shut down and in some cases excavation resulting in the high expenses encountered. As a consequence, such inspections are conducted at periodic intervals rather than continuously. Depending on the size of the interval, however, significant degradation can occur between inspections that can in turn result in unanticipated failures. A common method for inspection of gas transmission pipelines is the use of in-line inspection tools (pigs). A key problem with using pigs is that around 30% of natural gas transmission pipelines in United States are not piggable due to various constraints, such as sharp bends, diameter changes, and valving systems.

In-line inspections of gas transmission pipelines are primarily carried out to measure pipeline wall thickness changes resulting from corrosion and dents resulting from third party damage. According to the US Department of Transportation Office of Pipeline Safety (OPS), internal corrosion caused about 15 percent of all gas transmission pipeline reportable incidents over the last two years, leading to an average of $3 million in annual property damage. Furthermore, fatalities have occurred at pipeline failures associated with internal corrosion. Efforts have therefore been made at developing methods to predict the location of corrosion within pipelines that then reduce the number of sites that require actual physical inspection (either using pigs or through excavation). This method has been termed internal corrosion direct assessment (ICDA).

Though ICDA does prioritize the locations for further pipeline inspections and possible excavation, it does not provide a direct measure if water is actually present at those locations nor does it determine if corrosion is occurring. Pipelines still must be inspected and if the pipe segment is unpiggable, then the pipe needs to be excavated to detect and monitor corrosion.

Another common maintenance problem encountered in gas pipelines, especially in gas distribution systems, is leak detection. Leaks are often due to third party damage, which occurs when construction or excavation crews inadvertently strike underground utility lines. Natural gas distribution systems are constructed using pipes made of either steel or plastic. The utility companies will use manual inspection methods to look for leaks in sections of pipe line. Existing methods are labor intensive and the leak information not timely.

Thus, there is a need for a method and a system for detection of internal corrosion inside metal pipelines that will complement the ICDA method. Furthermore there is a need for remote and real-time monitoring of any type of gas pipelines. Once such a system is in place then gas pipelines can be monitored for corrosion, humidity, gas mixture, gas flow rates and pressure.

Wireless transmission of electromagnetic radiation communication signals has become a popular method of transmitting RF signals, such as cordless, wireless, and cellular telephone signals, pager signals, two-way radio signals, etc. There is, however, no system in place to transmit information using wireless inside gas pipelines.

BRIEF SUMMARY OF THE INVENTION

An embodiment of the present invention provides a method and system for in-situ inspection of pipelines with a low power wireless sensor network that are small, low cost, and rugged. The system includes a device for introducing electromagnetic radiation into the pipeline such that the pipe acts as a wave-guide for the electromagnetic radiation. The system includes a network of nodes to transmit and receive data between access points in the pipeline. The system further includes a device for enabling the electromagnetic radiation to propagate beyond the pipeline to a computer or to the Internet. The system may be configured to consume so little power that it can operate from a small internal battery for years. The low cost and ease of installation provides a viable solution for managing pipelines.

The present invention also includes the method and system for establishing a sensor network in existing pipelines and new pipelines, then extracting the sensor data using a wireless system followed by a recommendation of maintenance and repair of the pipeline based on the sensor data, historical data and other theoretical predictive models. This invention also includes the method for delivery of sensors inside the pipeline.

The present invention also includes corrosion sensors to detect internal corrosion inside metal pipes and a multitude of sensors for detection of leaks.

The present invention represents a substantial advance over prior systems and methods for monitoring pipelines. Because the present invention utilizes low cost wireless devices called motes, the present invention has the advantage that it is relatively inexpensive. The present invention also has the advantage that it does not require the extensive use of wires or cables to transmit the communication signals. These advantages, and other advantages and benefits of the present invention, will become apparent from the Detailed Description of the Invention herein below.

BRIEF DESCRIPTION OF THE DRAWINGS

For the present invention to be clearly understood and readily practised, the present invention will be described in conjunction with the following figures, wherein.

DETAILED DESCRIPTION OF THE INVENTION

While the present invention will be described more fully it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

First briefly in overview, the present invention involves the establishing of a sensor network in existing gas pipelines (both transmission and distribution) and new pipelines, then collecting the sensor data from multiple sites for input into a recommendation engine that provides maintenance alerts for repair of the pipeline. The system may be more easily understood by its use in gas pipelines with the understanding that the foregoing is also broadly applicable in other domains. There are some 800,000 miles of gas transmission pipelines in continental US that require maintenance and as the infrastructure ages the need for constant monitoring of the pipelines will increase. Maintenance includes detection of leaks and prevention of catastrophic failures as a result of internal corrosion. In-line inspection tools provide a direct detection of internal corrosion however, due to various constraints such as sharp bends, diameter changes, and valving systems a significant portion of gas pipelines cannot be inspected using such techniques.

Figure 1:
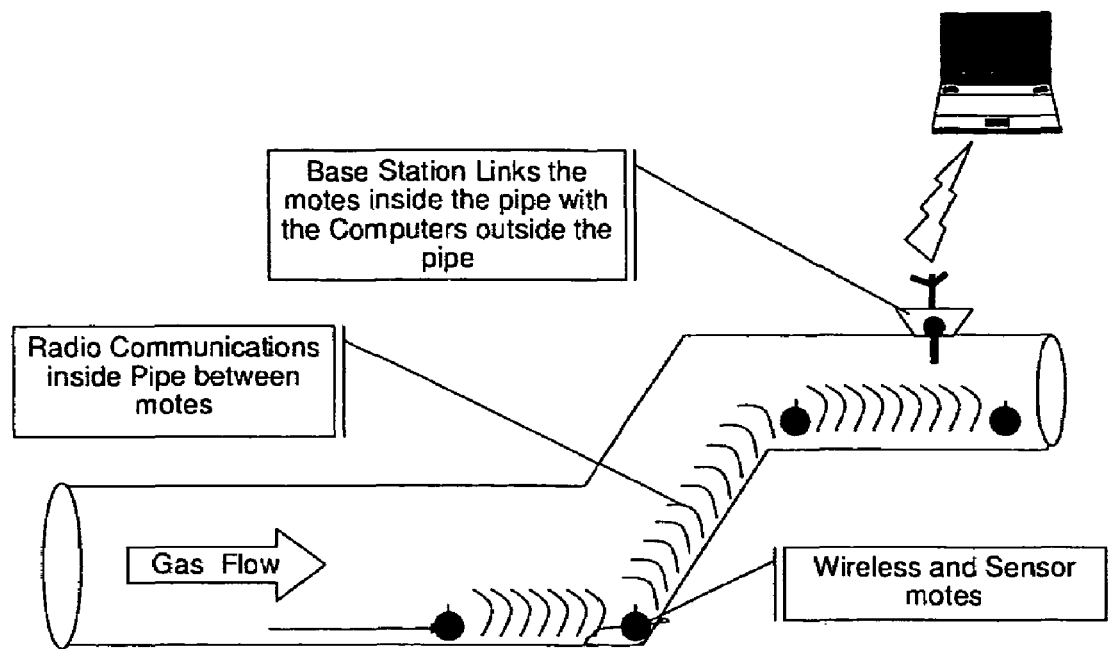
FIG. 1 is a diagram illustrating a gas pipeline with the wireless sensor network.

FIG. 1 illustrates a portion of a gas pipeline and a wireless sensor network. Communication signals and gas are transmitted through the pipeline, which acts as a waveguide for the communication signals. The pipeline exhibits those properties that are common to waveguides. The properties are detailed in R. Collin, "Field Theory of Guided Waves", 2d ed., IEEE, Press, N.Y. 1991, which is incorporated herein by reference. The wireless sensor network can utilize any type of metal or an electrically opaque material, such as, for example, steel or cast iron.

Figure 2:
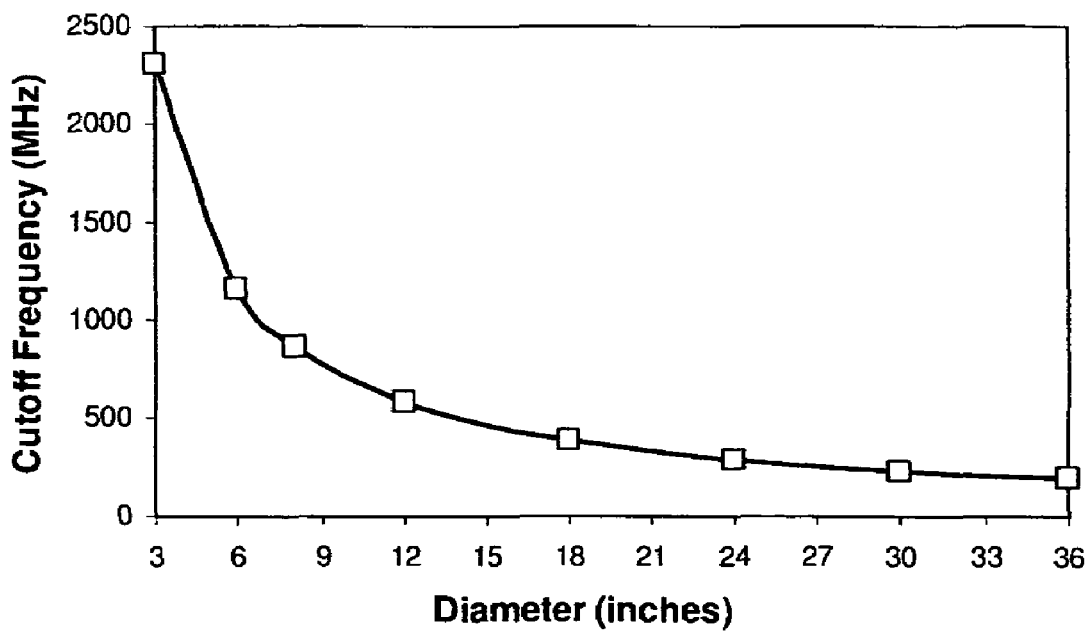
FIG. 2 is plot of the cutoff frequencies versus the radius of the pipe.

The current invention proposes using a low power wireless sensor network that use motes, which are wireless transceivers with well defined I/O and standard antenna connectors, integrated with micro sensors. Motes communicate with each other to pass the sensor data to an access point in the pipeline. FIG. 2 depicts the minimum frequency required for wireless transmission in pipes at various pipe diameters. The pipe behaves as a multimode waveguide at Industrial, Scientific, and Medical (ISM) band frequencies (902-928 MHz, 2.4-2.4835 GHz, 5.15-5.35 GHz, and 5.725-5.825 GHz).

In general, the antenna used on the mote may be any transducer capable of converting electrical into wireless broadcast signals. Examples of transducers include antennas, such as those typically used in wireless radio frequency (RF) communications; electrical-optical converters, such as light emitting diodes, lasers, photodiodes; and acoustic devices, such as piezoelectric transducers. In a preferred embodiment, the antenna is an electrical antenna, designed for operation in the frequency range between 30 MHz and 3,000 MHz, generally known as the ultrahigh frequency (UHF) band. The UHF frequency band is particularly well suited to the pipeline application because UHF circuits and components are relatively small in size and consume relatively low power. For example, physical limitations in antenna construction typically result in antennas being scaled to approximately one-half the wavelength of operation. The half-wavelength ranges from 5 meters to 5 cm in the UHF band.

In a particularly preferred embodiment, the antenna is a microstrip patch antenna operating within the frequency range of 2.4-2.4835 GHz. Microstrip patch antennas are relatively small compared with other resonant antennas, such as dipole antennas, operating over the same frequency range. Microstrip patch antennas are also rugged, easily designed and fabricated and relatively inexpensive. Although it may be desirable to operate at even higher frequencies, other considerations, such as government regulation, may stand in the way. For example, transmitting RF signals within certain frequency bands may be prohibited altogether, while use of other frequency bands may be restricted to special users, such as airlines or the military. Operation within the 2.4 GHz to 2.4835 GHz frequency band is largely available for industrial, science and medical applications.

Figure 3:
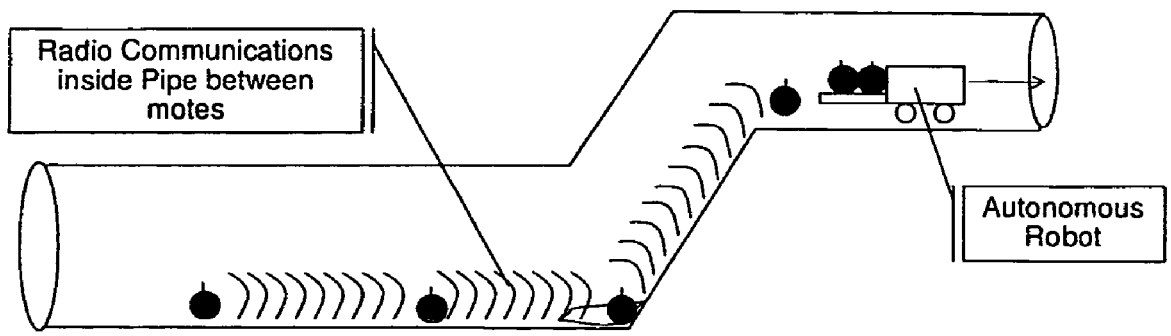
FIG. 3 is a diagram of the spherical sensor mote package being deployed inside the pipelines and FIG. 4 is a diagram of the integrated wireless transceiver and sensor inside self contained environmentally sealed spherical package.
Figure 3:
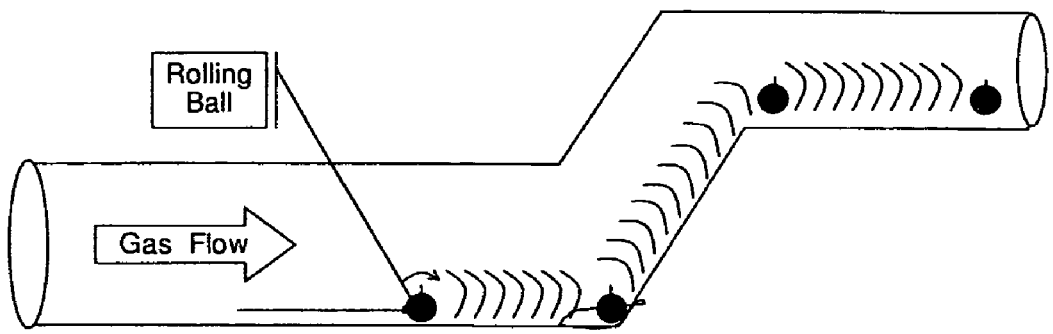

FIG. 3 depicts the spherical package containing the wireless transceiver and the sensors delivered to the point of inspection either through the gas stream or by rolling it along the pipeline walls or using robots. The wireless network is then established and configured using a mesh network consisting of a "mesh" of interconnected wireless devices. Nodes on mesh networks must have at least two viable routes at all times, and be able to support multiple hops between source and destination. Redundant routes ensure resiliency in case of offline nodes or broken links, and multi-hopping permits granular route optimization and simplified installation. Multi-hop routing also reduces the power required to transmit a packet between source and destination. Using a multi-hop network saves battery power by handing off data from mote to mote rather than blasting out a higher-power RF signal. The network consists of a base station or a network manager that provides management and quality of service functions for a network of motes. The manager coordinates routing, aggregates mote packets, and also collects statistics of the mote network. A mesh network can be created by the mote hardware and software available from several vendors such as supplied by Dust Networks in Berkeley, Calif. or by Crossbow Technologies in San Jose, Calif.

The type of sensor will depend on the parameter being measured. To detect leaks ultrasonic flow sensors and pressure sensors are used and to measure internal corrosion a variety of corrosion sensing devices can be deployed. These include for example multi-electrode array sensors, galvanic couple sensors, and electrical resistance probes. In addition, humidity, pH, and temperature sensors can also be monitored. These can be used individually or in combination on one chip (sometimes also called "Lab-on-Chip"). The sensors can be used in combination to detect leaks or corrosion. The sensor information is typically available as baseband electrical signals, such as voltage or current levels, or sequences of binary digits, or bits, of information.

Figure 4:
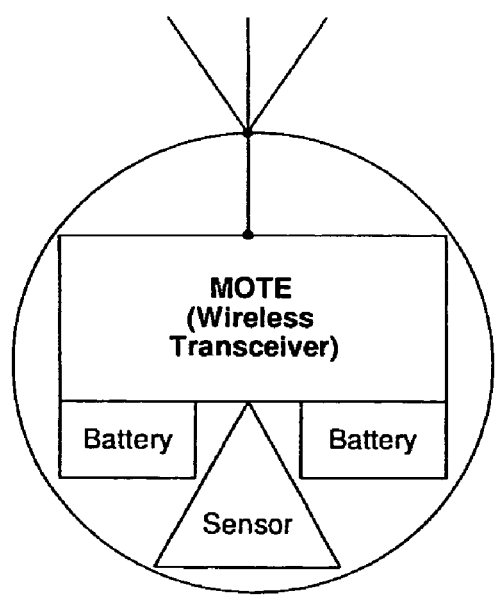

In more detail, referring to FIG. 4, one embodiment of a mote-sensor system includes the wireless transceiver with the sensor in a spherical package. The sensors and the mote are also connected to a power source. The packaging can be of other shapes, such as an egg shape with a flat bottom to ensure that the antenna is always facing towards the axis of the pipe or a dome shape. The sensing probe of the corrosion sensor should be facing the pipe walls. Small magnets can be used to attach the mote sensor system to the pipe walls.

In this application, it is advantageous for each of the sensors to provide some form of identification allowing the base station (or manager) to distinguish which sensor is reporting. Identification means may include broadcasting a unique address tone, or bit sequence, broadcasting in a pre-assigned time slot, or broadcasting on an allocated frequency.

The sensor information and processed sensor information may be made available on the Internet through a Web server application. In one embodiment, a web application may be provided offering access to information for monitoring purposes. The application may respond to web client requests for temperature, humidity, corrosion, and flow rate information. Alternatively, alerts can be provided based on predefined set of rules such as on detection of leaks or on detection of significant corrosion. The data collected from the sensor can be used directly for determining maintenance and repair. A recommendation engine can further aid in the monitoring by using data from historical maintenance and repair records, theoretical and predictive models for damage propagation, and sensor data from the wireless sensor network. The recommendation engine can be based on statistical models or bayesian networks or similar techniques that provide intelligence.

Another embodiment of the invention is determining the location of the sensor for repair and maintenance. Standard GPS techniques cannot be used to determine location, as the radio signals used in this invention cannot penetrate metal pipe walls. Using a combination of ultrasound and RF signals the location can be determined to the accuracy of couple of centimeters. Crossbow Technology from San Jose, Calif. offers this "Cricket Mote" a location-aware mote module. Alternatively, if robots are used for deployment of the sensor network, then inertial sensors can be used to accurately map the pipeline as it traverses, including noting the location where the motes and sensors are dropped. The robot equipped with optical encoders measures distance traveled as the vehicle passes through the pipe. By placing encoders on several wheels on different locomotion units, the effect of slip and loss of traction in joints can be minimized. The equipped with an inclinometer module to provide precision tilt with range up to .+−.50.degree. with 0.3.degree. resolution. The output provides the tilt angles relative to Earth's gravity, known as the pitch and roll angle. The inclinometer provides a solid-state solution to tilt compensation, eliminating all mechanical impediments to performance. A rear-facing sensor on the robot will accurately measure distance to the deployed communication/navigation nodes to constantly update the vehicle's internal odometry.

The invention claimed is:

1. A method for monitoring for maintenance and repair of gas pipelines made of metal for detection of internal corrosion that can result in leaks causing catastrophic failures, the method comprising: providing corrosion sensors for detection of internal corrosion; providing a wireless sensor network, comprising several wireless transceivers, that collect the sensor data from multiple sites and provides maintenance alerts for repair of the pipelines; establishing the wireless sensor network inside the pipelines using a method for delivery of the sensors to the site; activating the sensors to make measurements periodically or continuously; extracting the corrosion sensor data from the sensors using a the wireless network to access points in the pipelines and analyzing sensor data using a recommendation engine.

2. The method of claim 1 wherein the wireless sensor network uses wireless transceivers with well defined I/O and standard antenna connectors capable of forming a mesh network or a star network.

3. The method of claim 1 wherein the wireless network operates inside pipes such that the gas pipelines (made of metal act as a waveguide for the electromagnetic radiation.

4. The method of claim 1 wherein sensors for detection of internal corrosion including a multi-electrode array sensor, a galvanic sensor, interdigitated corrosion sensors or an electrical resistance probe.

5. The method of claim 1 wherein corrosion sensors and said wireless transceivers are sealed in a package for operation inside said gas pipelines.

6. The method of claim 1 wherein the sensors are programmed, configured and controlled at a remote server computer through a base station.

7. The method of claim 1 wherein analyzing sensor data using said recommendation engine includes the use of statistical models or Bayesian networks.

8. A method for deploying a wireless sensor network inside gas pipelines comprising the steps of: identifying locations for inspection using a sealed package containing a sensor or sensors and wireless transceivers; transporting the package containing the wireless transceiver and sensors to the identified sites; determining a physical co-ordinates of where the inspection takes place using a wireless signal; and activating the wireless sensor network through a base station.

9. The method of claim 8 wherein the sealed package is transported to the inspection site using an autonomous robot.

10. The method of claim 8 wherein the sealed package is transported to the inspection site by rolling it inside the pipeline.

11. The method of claim 8 wherein the location of the inspection sites is determined using signal strength and time difference of arrival of the wireless signal.

12. The method of claim 8 wherein the location of the inspection sites is determined by an autonomous robot equipped with an inertial sensor.

* * * * *